(12) United States Patent
Klinger et al.

(10) Patent No.: US 11,225,546 B2
(45) Date of Patent: Jan. 18, 2022

(54) PROCESS FOR PREPARING ISOCYANATES

(71) Applicant: Dow Global Technologies LLC, Midland, MI (US)

(72) Inventors: Artur Klinger, Stade (DE); Paul A. Gillis, Lake Jackson, TX (US); Irfan Khan, Houston, TX (US)

(73) Assignee: Dow Global Technologies LLC, Midland, MI (US)

( * ) Notice: Subject to any disclaimer, the term of this patent is extended or adjusted under 35 U.S.C. 154(b) by 319 days.

(21) Appl. No.: 16/491,922

(22) PCT Filed: Feb. 28, 2018

(86) PCT No.: PCT/US2018/020088
§ 371 (c)(1),
(2) Date: Sep. 6, 2019

(87) PCT Pub. No.: WO2018/164894
PCT Pub. Date: Sep. 13, 2018

(65) Prior Publication Data
US 2021/0139637 A1 May 13, 2021

Related U.S. Application Data

(60) Provisional application No. 62/467,317, filed on Mar. 6, 2017.

(51) Int. Cl.
*C08G 18/76* (2006.01)
*B01F 5/04* (2006.01)
(Continued)

(52) U.S. Cl.
CPC .......... *C08G 18/7664* (2013.01); *B01F 5/048* (2013.01); *C07C 263/10* (2013.01); *C07C 265/14* (2013.01)

(58) Field of Classification Search
None
See application file for complete search history.

(56) References Cited

U.S. PATENT DOCUMENTS 7,901,128 B2 3/2011 Gehrke et al.
8,816,126 B2 8/2014 Mattke et al.
(Continued)

FOREIGN PATENT DOCUMENTS

WO 2011/115849 A1 9/2011
WO 2013/029918 A1 3/2013
(Continued)

OTHER PUBLICATIONS

PCT/US2018/020088, International Search Report and Written Opinion dated Jun. 7, 2018.
(Continued)

*Primary Examiner* — Ha S Nguyen

(57) ABSTRACT

A process for preparing an isocyanate product includes providing a phosgene inlet stream and an amine in solvent inlet stream to a phosgenation mixer, the amine in-solvent inlet stream including one or more amines and one or more inert solvents, and during steady state operation compensating for a fouling pressure drop increase by decreasing a pressure drop in the phosgenation mixer over a time period divided into at least a first period of time T1 and a second period of time T2 that is subsequent to the first period of time T1. During the second period of time T2 an amine concentration of the one or more amines in the amine-in-solvent stream is higher than during the first period of time T1, and during the second period of time T2 a phosgene-to-amine ratio value in the phosgenation mixer is higher than during the first period of time T1.

10 Claims, 4 Drawing Sheets

(51) Int. Cl.
*C07C 263/10* (2006.01)
*C07C 265/14* (2006.01)

(56) References Cited

U.S. PATENT DOCUMENTS

| | | |
|---|---|---|
| 9,090,540 B2 | 7/2015 | Merenov et al. |
| 2012/0095255 A1 | 4/2012 | Mattke et al. |
| 2013/0060062 A1* | 3/2013 | Mattke .................. C07C 263/10 560/347 |
| 2013/0176814 A1 | 7/2013 | Gillis et al. |
| 2015/0018575 A1 | 1/2015 | Gillis et al. |

FOREIGN PATENT DOCUMENTS

| | | | | |
|---|---|---|---|---|
| WO | WO-2013029918 A1 * | 3/2013 | ........... | C07C 263/10 |
| WO | 2015/144658 A1 | 10/2015 | | |

OTHER PUBLICATIONS

PCT/US2018/020088, International Preliminary Report on Patentability dated Sep. 19, 2019.

* cited by examiner

PROCESS FOR PREPARING ISOCYANATES

FIELD

Embodiments relate to a process for preparing isocyanates and a system for the use of the process for preparing isocyanates.

INTRODUCTION

Isocyanates may be prepared by reacting amines with phosgene in an inert solvent. For example, the amine may be converted to an isocyanate by contacting the phosgene directly with the amine in a solvent. When preparing such isocyanates during a continuous operation, it is known that progressive fouling may occur. The system fouling may adversely affect the production rate and/or product quality. Accordingly, methods of compensating for system fouling, without a forced significant reduction in the production rate, increased energy consumption, and/or change in product quality are sought.

SUMMARY

Embodiments may be realized by providing a process for preparing an isocyanate product that includes providing a phosgene inlet stream and an amine-in-solvent inlet stream to a phosgenation mixer, the amine-in-solvent inlet stream including one or more amines and one or more inert solvents, and during steady state operation compensating for a fouling pressure drop increase by decreasing a pressure drop in the phosgenation mixer over a time period divided into at least a first period of time $T_1$ and a second period of time $T_2$ that is subsequent to the first period of time $T_1$. During the second period of time $T_2$ an amine concentration of the one or more amines in the amine-in-solvent stream is higher than during the first period of time $T_1$, and during the second period of time $T_2$ a phosgene-to-amine ratio value in the phosgenation mixer is higher than during the first period of time $T_1$.

BRIEF DESCRIPTION OF THE DRAWINGS

Features of the embodiments will become more apparent to those of ordinary skill in the art by describing in detail exemplary embodiments thereof with reference to the attached drawings in which.

DETAILED DESCRIPTION

Figure 1:
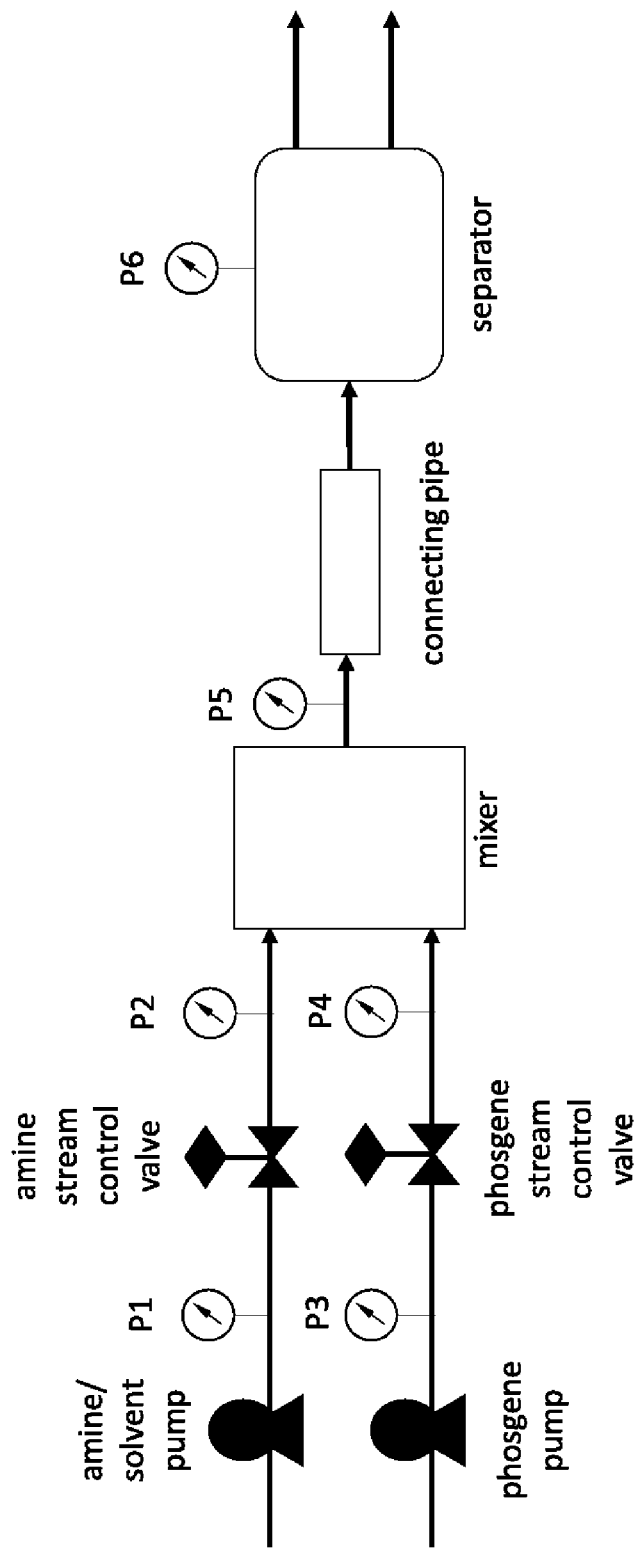
FIG. 1 illustrates an exemplary system for the production of isocyanates.

Embodiments relate to a phosgenation process (such as a liquid phase process and/or a gas phase process) usable in a process for preparing isocyanates and a system that utilizes the phosgenation process. The process and system enable having a specified product quality value (e.g., a predetermined impurity level range) for the resultant isocyanate product and avoids significant forced reductions in a production rate for the isocyanate product. The composition of an amine-in-solvent inlet stream, a flow rate of the amine-in-solvent inlet stream, and/or a flow rate of the phosgene inlet stream are adjustable in the process and operation of the system for the production of isocyanates.

During steady state operation of a continuous process for preparing such isocyanates, the energy available to mix the amine-in-solvent stream and the phosgene stream may be maximizing by minimizing pressure drop in a control valve upstream of the amine-in-solvent stream and increasing the pressure drop in the phosgenation mixer. This may result in a reduction of the range of volumetric flow rate of the amine-in-solvent stream (e.g., based on an increase in fouling pressure drop), which can be compensated by varying the amine concentration and phosgene-to-amine ratio over a period of time divided into at least a first period T1 and a second period T2 that is subsequent to the first period of time T1. Maximizing the pressure drop in the phosgenation mixer may allow for overall improved performance of the process that can be leveraged to either improved quality or increased production rate or reduced energy cost. For example, both production rates and product quality values may be maintained, e.g., by increasing a phosgene stream flow rate while decreasing solvent flow in an amine-in-solvent inlet stream.

By pressure drop it is meant the difference in pressure between a first point in the system for preparing isocyanates and a second point in the system. For example, pressure drop across the phosgenation mixer may be determined between a first point in the process before the phosgenation mixer and at a second point in the process after the phosgenation mixer. For amine side pressure drop for the phosgenation mixer, the first point may be measured near a point where the amine-in-solvent inlet stream enters the phosgenation mixer and the second point may be measured in the reaction stream that exists phosgenation mixer (e.g., the second point may be in the corresponding piping or in a further downstream separator connected to the piping). Fouling pressure drop may be determined as frictional and/or turbulence dissipation pressure drops across the piping (also referred to as total pressure drop across the piping) in which fouling is occurring, e.g., the piping leading from the phosgenation mixer to a downstream separator. The increased fouling pressure drop may occur based on contraction and expansion losses as the flow passes a constriction in the piping due to local fouling and/or from increased frictional pressure drop based on surface roughness and/or area changes.

By production rate it is meant the isocyanate product output for the system, e.g., the amount per a period of time of PMDI production from the plant. A specified production rate allows for deviations of ±5% from the set production rate. The production rate may be set as a percentage, with 100% being the specified production rate. According to embodiments, during the process for preparing isocyanates, the production rate may be set as a relatively constant value even as progressive fouling occurs in the system. The production rate may be set as a relatively constant value, which phrase relatively constant allows for deviations ±5% from the specified value.

By specified product quality it is meant that the production process and system are ran with a specified value for a plant specific quality measure. The specified product quality allows for relative deviations of ±10% from the specified product quality value, which is also referred to as the specified product quality value range. The specified product quality may be a measure (e.g., weight percent based measure) of amounts of specific impurities in a product stream and may be referred to as an impurity level. Such as in the production of polymeric methylene diphenyl diisocyanate (PMDI) the specified product quality may be a measure of certain undesirable components in a specific stream in the process for forming isocyanates. In exemplary embodiments, the specified product quality may measure the loss of isocyanate groups by the formation of certain by-products, such as by-products formed by the reaction of one isocyanate group with another isocyanate group. Examples of such by-products include those with carbodiimide formation, uretonimine formation, and/or uretdione formation. According to embodiments, during the process for preparing isocyanates, the specified product quality may be set as a relatively constant value, which phrase relatively constant allows for deviations ±10% from the specified value, even as progressive fouling occurs in the system.

By normal operation it is meant during steady state operation, which is distinguished from start-up operation, shut-down operation, and turn down operation. For example, normal operation starts after start-up operation has finished and/or ends before shut-down operation or turnover operation has started. The steady state operation includes operation above nominal capacity of the phosgenation mixer. The steady state operation may include operation below maximum capacity of the phosgenation mixer.

Referring to FIG. 1, during a phosgenation process, at least two inlet streams (e.g., liquid streams) are feed to a phosgenation mixer. The amine-in-solvent inlet stream includes at least an amine/solvent pump and an amine stream control valve. A first pressure point P1 relates to the pressure at a point between the amine/solvent pump and the amine stream control valve. A second pressure point P2 relates to the pressure at a point between the amine stream control valve and the phosgenation mixer. The phosgene inlet stream includes at least a phosgene pump and a phosgene stream control valve. A third pressure point P3 relates to a pressure between the phosgene pump and the phosgene stream control valve. A fourth pressure point P4 relates to a pressure between the phosgene stream control valve and the phosgenation mixer. At least one combined reaction stream exists the phosgenation mixer and is feed to a separator, e.g., for separating an unreacted phosgene stream from an isocyanate product stream. A fifth pressure point P5 relates to a pressure between the phosgenation mixer and the separator, e.g., in a connecting pipe therebetween. A sixth pressure point P6 relates to a pressure in the separator. According to exemplary embodiments, amine side pressure drop across the phosgenation mixer, may be measured between pressure point P2 and pressure point P5. Fouling pressure drop may be determined measured between pressure point P5 and pressure point P6. Each pressure point may independently correspond to a pressure measurement device such as a pressure sensor and/or a point where a pressure measurement in taken manually.

Typically, in a phosgenation process, normal operation may run at a constant, with respect to composition and flow rate, for the inlet streams. Gradually at least an upstream control valve (such as the amine stream control valve) may be opened as fouling increases in a corresponding piping connection leading from the phosgenation mixer to the separator. During such an operational procedure, pressure drop changes due to fouling are only addressed by the upstream control valves, such that the overall pressure drop in the overall system may drastically vary. However, improved methods of producing isocyanates are sought, with a view toward maintaining a predetermined product quality value, production rate and/or avoid substantial increased energy consumption are sought. For amine side pressure drop for the phosgenation mixer, the first point may be measured near a point where the amine-in-solvent inlet stream enters the phosgenation mixer and the second point may be measured in the reaction stream that exists phosgenation mixer (e.g., the second point may be in the corresponding piping or in a further downstream separator connected to the piping). Fouling pressure drop may be determined as total pressure drop across the piping in which fouling is occurring, e.g., the piping leading from the phosgenation mixer to a downstream separator.

According to embodiments, in the phosgenation process, normal operation may include initially using a higher pressure drop phosgenation mixer, e.g., the initial pressure drop for the amine side of the phosgenation mixer may be higher than what is seen in a typical phosgenation process. The initially higher pressure drop phosgenation mixer may be provided with comparatively smaller jets for the amine-in-solvent inlet stream. The initially higher pressure drop imparts higher energy to the mixer at the onset of steady state operation of the system, which allows for improved mixing that can be turned into lower utility costs, better quality, and/or higher production. Accordingly, the initial higher pressure drop can be used as a tool in the overall process that relies on adjusting various parameters to maintain a relatively constant product quality and production rate. Subsequently, as decreasing pressure drop in the phosgenation mixer is realized, such pressure drop may be used to compensate for increases in fouling pressure drop downstream, while still maintaining a relatively constant product quality and production rate.

Further, during normal operation an amine concertation in the amine-in-solvent inlet stream and a phosgene-to-amine ratio (i.e., PAR) value may be adjusted, so as to maintain a predetermined production rate and product quality value for the isocyanate product stream. The PAR value may be changed by adjusting the flow rate of the phosgene inlet stream and/or changing the amount of amine entering the phosgenation mixer. For example, the flow rate of the phosgene inlet stream may be changed to maintain production quality even as other parameters such as amine side pressure drop in the phosgenation mixer in the process of production of isocyanates is changed.

In combination with using the initially higher pressure drop phosgenation mixer, the initial pressure drop attributed to the amine/solvent control valve may be less relative to the typical phosgenation process discussed above. Then, as normal operation progresses, the composition of the amine-in-solvent inlet stream may be changed by increasing the concentration of the amine by decreasing the solvent flow rate, with respect to forming the amine-in-solvent inlet stream. The overall flow rate of the amine-in-solvent inlet stream may be kept the same or changed, but overall the concertation of amine entering the phosgenation mixer in the amine-in-solvent inlet stream is increased. In exemplary embodiments, the composition of the amine-in-solvent inlet stream may be adjusted such that as the amount of solvent is decreased and the amine concentration is increased, the overall flow rate of the amine-in-solvent stream may be decreased (e.g., as system fouling increasing). In another exemplary embodiment, an overall flow rate of the amine-in-solvent stream is unchanged. As the amine concentration in the amine-in-solvent inlet stream is increased, the phosgene flow rate may be the same or changed.

Accordingly, a specific combination of the initially higher pressure drop phosgenation mixer, the higher amine concentrations, and the higher PAR values may allow the isocyanate production plant to maintain a relatively constant production rate and product quality value, even while progressive fouling is occurring in piping downstream of the phosgenation mixer. In other words, embodiments relate to a system, process, and procedure for maximizing energy savings while trying to maintain relevantly constant production rates and product quality value, while the progressive foul occurs in the system.

Phosgenation Mixer

A static mixer usable as a phosgenation mixer may be designed to incorporate a method for delivering two streams of fluids therein. As the streams move through the static phosgenation mixer, continuously blending of the materials is enabled. An exemplary static mixer usable as phosgenation mixer in the process for the production of isocyanates is illustrated in FIG. 2.

Figure 2:
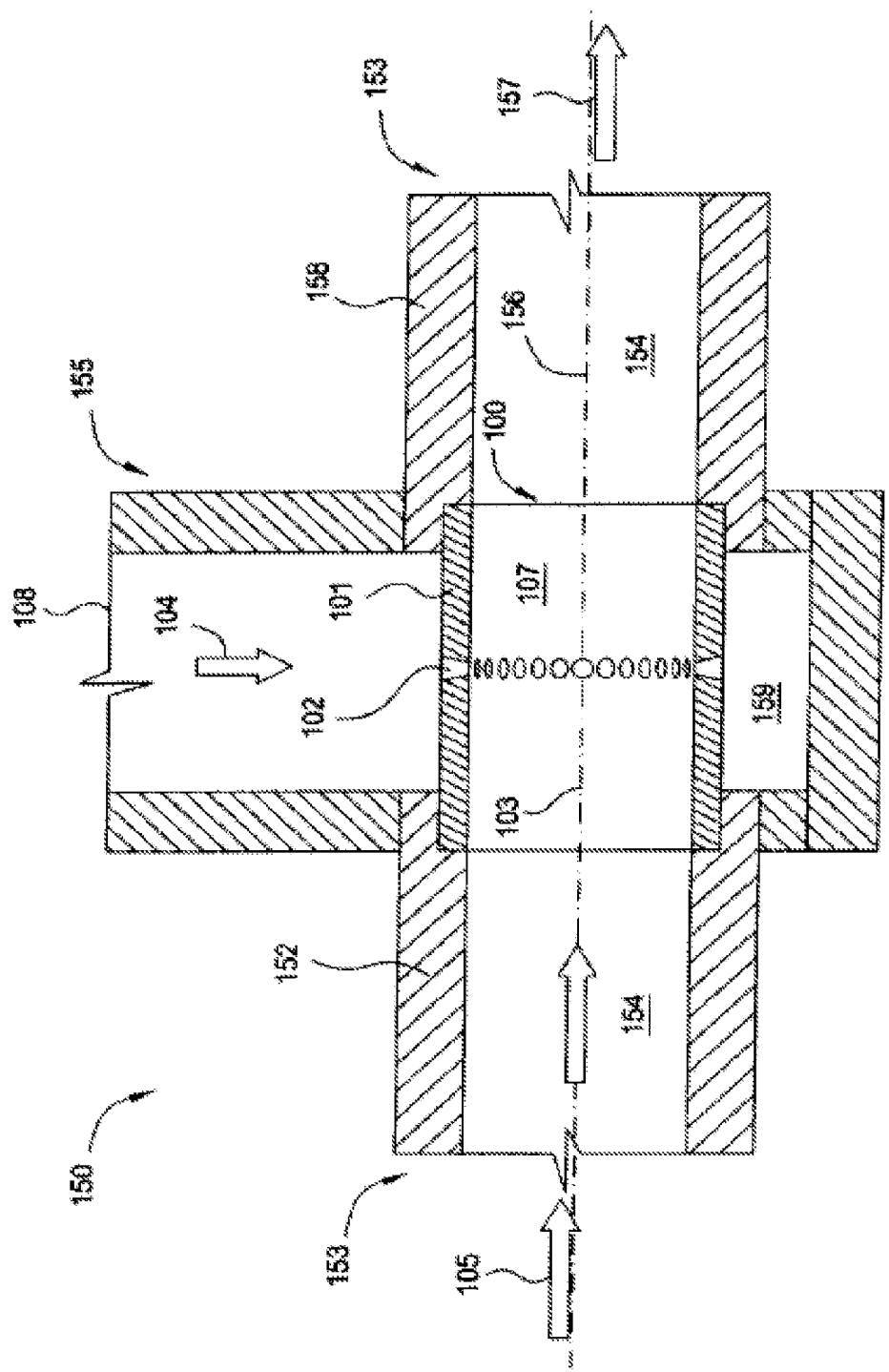
FIG. 2 illustrates an exemplary phosgenation mixer usable in an exemplary system for the production of isocyanates.

In particular, FIG. 2 illustrates a sectional view of an exemplary static mixer 150. The static mixer 150 includes a first flow conduit 153 defining an inner volume 154 which allows a first flow 105 therethrough along a longitudinal axis 156. The first flow 105 enters the static mixer 150 from the inlet end 152 flowing through the inner volume 154 towards the outlet end 158. The first flow 105 may be the phosgene inlet stream.

Referring to FIG. 2, the first flow conduit 153 includes an inlet end 152 and an outlet end 158. A mixing conduit 100 is coupled between the inlet end 152 and the outlet end 158 of the first flow conduit 153. The mixing conduit 100 includes a sidewall 101 surrounding (e.g., enclosing) a central axis 103 of the mixing conduit 100. The mixing conduit 100 may be positioned so that the central axis 103 coincides with the longitude axis 156 of the first flow conduit 153. The sidewall 101 defines an inner volume 107 of the mixing conduit, which may be co-axial with the inner volume 154 of the first-flow conduit 153. A plurality of jet openings 102 are formed through the sidewall 101 fluidly connecting the inner volume 107 of the mixing conduit 100 to an exterior of the mixing conduit 100.

Referring to FIG. 2, a second flow conduit 155 is attached to the first flow conduit 153. The second flow conduit 155 is coupled to the inlet end 152 and the outlet end 158 of the first flow conduit 153 and defines an annular chamber 159 surrounding the mixing conduit 100. The annular chamber 159 allows a second flow 104 to enter the inner volume 107 of the mixing conduit 100 through the plurality of jet openings 102 and to mix with the first flow 105. The second flow 104 may be the amine-in-solvent inlet stream. The mixing conduit 100 isolates the first-flow conduits 153 from the second-flow conduit 155, such that that the second flow 104 is restricted to mixing with the first flow 105 via the plurality of jet openings 102 in the mixing conduit 100. The second flow 104 enters the static mixer 150 at an inlet 108 of the second flow conduit 155 to the annular chamber 159 and then enters the inner volume 107 of the mixing conduit 100 to mix with the first flow 105 through the plurality of jet openings 102. A mixed flow 157 exits the static mixer 150 through the outlet end 158 of the first-flow conduit 153.

The parameters and structures of mixing conduits usable as a phosgenation mixer may be designed to obtain a desirable mixing result. For example, while the number of jet openings is limited by the diameter of the conduit and the diameter of the jet openings, to form a higher pressure drop static mixer, the diameter of the jets openings may be decreased without changing the overall number of the jet openings or the diameter of the conduit. As discussed in U.S. Patent Publication No. 2015/0018575, a mixing conduit of a static mixer may include 2 or more jet openings, 22 or more jet openings, from 22 to 50 jet openings, etc. The diameter of the jet openings may be from 1 mm to 10 mm (e.g., from 2 mm to 7 mm, from 3 mm to 5 mm, etc.). As discussed in U.S. Patent Publication No. 2013/0176814, a mixing conduit of a static mixer may include one or more flow obstructions disposed in an inner volume thereof. Each flow obstruction may be aligned upstream from an associated jet opening. As discussed in U.S. Pat. No. 7,901,128, a mixing conduit may have at least one tapered jet opening. A mixing conduit may use a plate type design to accomplish mixing through the use of intense turbulence in the flow. The static mixer elements may include a series of mixing elements (e.g., non-moving baffles) made of metal or a variety of plastics.

Preparation of Isocyanates

The production of various isocyanates includes a phosgenation stage. Exemplary isocyanates include polyisocyanates such as diphenyl methylene diisocyanate (MDI), toluene diisocyanate (TDI), isophorone diisocyanate (IPDI) and xylene diisocyanates (XDI), and modifications thereof.

For the production of the isocyanates, the amine-in-solvent stream includes an amine component that includes one or more amines and a solvent component that includes one or more solvents. The amine component may include one or more selected from methylamine, ethylamine, butylamine, stearylamine, phenylamine, p-toluidine, 1,4-diaminobutane, 1,6-diaminohexane, 1,8-diaminooctane, 1,4-diaminobenzene, 2,4- and/or 2,6-diaminotoluene, 2,2'-diaminodiphenylmethane, 2,4'-diaminodiphenylmethane, 4,4'-diaminodiphenylmethane, alkyl substituted diamines of the diphenylmethane series, polyamine mixtures of the diphenylmethane series as are obtained in a known manner by aniline-formaldehyde condensations, p-xylenediamine, perhydrogenated 2,4-diaminotoluene, perhydrogenated 2,6-diaminotoluene, 2,2'-diaminodicyclohexylmethane, 2,4'-diaminodicyclohexylmethane, 4,4'-diaminodicyclohexylmethane, 1-amino-3,3,5-trimethyl-5-aminomethylcyclohexane, the ethyl ester of lysine, the aminoethyl ester of lysine, 2,4-toluenediamine, 2,6-toluenediamine, 1,6,11-triaminoundecane, and mixtures thereof.

The solvent component may include one or more of inert solvent, e.g., a non-halogenated aromatic hydrocarbon (such as toluene and/or xylene), a halogenated aromatic hydrocarbon (such as a chlorinated aromatic hydrocarbon), and mixtures thereof. Exemplary halogenated aromatic hydrocarbons include chlorobenzene and chloroethybenzene, for both of which various structures are included, examples include monochlorobenzene, dichlorobenzenes, and trichlorobenzenes.

A liquid-phase phosgenation process according to exemplary embodiments, may be usable in a process for the production of PMDI. The process may include forming methylene diphenyl diamines and polyamines of the diphenylmethane series by reacting aniline and formaldehyde in the presence of an acid catalyst, phosgenating the methylene diphenyl diamines and polyamines of the diphenylmethane series to produce a mixture of the MDI isomers and polymeric MDI, after which the mixture may be separated into various fractions, e.g., as discussed in U.S. Pat. No. 9,090,540. The methylene diphenyl diamines and polyamines of the diphenylmethane series that are formed may form the amine component in the amine-in-solvent inlet stream.

In an exemplary embodiments, during the process for producing an PMDI based product, when aniline with formaldehyde are reacted to form the methylene diphenyl diamines (and polyamines of the diphenylmethane series), at least the condensation reaction as shown below may be realized:

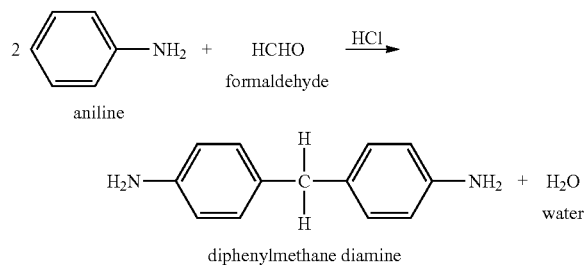

Suitable polyamine mixtures of the diphenylmethane series may be obtained by condensation of aniline and formaldehyde in a quantitative molar ratio from 20:1 to 1.6:1 and a quantitative ratio of aniline to acid catalyst from 20:1 to 1:1. Formaldehyde may be used as an aqueous solution with water content from 1 wt % to 95 wt % by weight, based on the total weight of the aqueous solution. Other compounds supplying methylene groups (e.g., polyoxymethylene glycol, para-formaldehyde, and/or trioxane) may be used, alone or in combination with formaldehyde. Strong acids, particularly inorganic acids, are suitable as acid catalysts for the reaction of the aniline and formaldehyde. Suitable acids include hydrochloric acid, sulfuric acid, phosphoric acid, and methane sulfonic acid. Solid acid catalysts, such as organic and inorganic ion exchangers, acid silicon/aluminum mixed oxides, and acid zeolites may also be used.

In exemplary embodiments, the aniline and the acid catalyst are first mixed together. The mixture of aniline and the acid catalyst are then mixed with formaldehyde at temperatures from 20° C. to 100° C., and a preliminary reaction is carried out. In other exemplary embodiment, aniline and formaldehyde are first mixed at temperatures from 5° C. to 100° C., in the absence of the acid catalyst. In such an example, condensation products of aniline and formaldehyde are formed (i.e., aminal). On completion of the aminal formation, water present in the reaction mixture may be removed by phase separation or by other suitable procedures, such as distillation. The condensation product is then mixed with an acid catalyst, and a preliminary reaction is carried out at a temperature from 20° C. to 100° C. In either case, the temperature of the reaction mixture is then raised, either in stages or continuously, to a temperature of from 100° C. to 250° C. The reaction mixture may then be neutralized with a base, such as hydroxides of alkali metals and/or alkaline earth metals (e.g., sodium hydroxide).

Then, the resultant product of the above process forms an amine stream to be used in the process for forming PMDI. In particular, in a phosgenation stage, at least the polymeric diphenylmethane diamine (also referred to as PMDA) may react with phosgene as shown below:

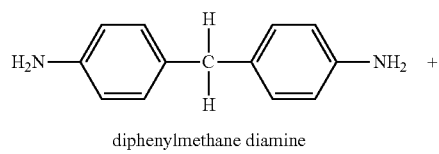

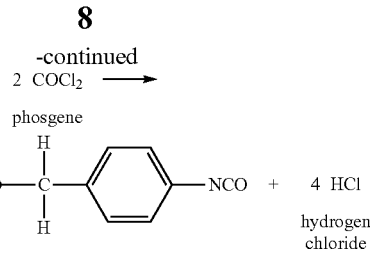

The above phosgenation process may be performed in the phosgenation mixer, according to exemplary embodiments. The phosgenation process may be carried out at temperatures from 50° C. to 250° C. The phosgenation process may be carried out at pressures from ambient pressure to 50 bar.

After the phosgenation process, the resultant mixture may be feed to a separator, during which the excess phosgene, inert organic solvent, the hydrogen chloride formed, and/or mixtures thereof, are separated from the reaction mixture. After the separation stage, the process may yield an isocyanate product that is referred to as PMDI, which may include a level of impurities. Such product mixtures may include three isomers of MDI, i.e., 4,4'-MDI, 2,4'-MDI, and 2,2'-MDI. Some tetramer and/or higher adducts may also be formed. This isocyanate product may be referred to as a final product and the product quality may be evaluated for the mixture. The production rate may be based on the output of the isocyanate product.

The isocyanate product may be further processed to form a purified isocyanate product, which may be recovered from the PMDI via a subsequent purification process. The purification process may include one or more separation methods, such as distillation, extraction, or crystallization. Dependent on the purification process used, different types of MDI based final products may be formed, such as monomeric MDI. Exemplary separation of the crude diisocyanate and polyisocyanate may be performed using various techniques, e.g., exemplary separation techniques are discussed in U.S. Pat. No. 9,090,540. In exemplary embodiments, the separation process may include one or more distillation columns and the product that contains the organic phase remaining after the separation may be subjected to a wash procedure to form a purified organic phase.

Production System

According to embodiments, in the system for the production of isocyanates, mechanical energy for the phosgenation mixer is shifted from an upstream control valve associated with the amine-in-solvent stream into the mixer by relying on pressure drop in the amine-in-solvent stream. Said in another way, the mechanical energy may be prevented from being lost in the upstream control value and instead is moved to the phosgenation mixer to maximize the energy to mix the amine-in-solvent stream and the phosgene stream. As such, the reliance on the upstream control valve for the mixing rates in the phosgenation mixer is decreased, while the reliance on pressure drop is increased, in an effort to maintain a relatively constant production rate (i.e., within ±5% of the specified production rate) and a relatively constant product quality value (i.e., within ±10% of a specified product quality value) during steady state operation. The mixing rates for the amine from the amine-in-solvent inlet stream and the phosgene from the phosgene inlet stream, may be related to product quality. For example, the formation of undesired by-products may be decreased as mixing rates are increased.

Adjustments are also made to the amine concentration in the amine-in-solvent stream and PAR values, as needed. Further, as a decrease in amine side pressure drop in the phosgenation mixer and an increase fouling pressure drop are realized, the two changes in pressure drop may compensation for each other and allow for maintaining an approximately constant pressure drop for the system. This system pressure drop, may allow for a longer periods of operation prior to requiring cleaning of the system. Further, such as design may allow for a reduction in energy usage by the plant. For example, operating a plant at certain PAR values may reduce the energy-intensive distillation of phosgene and/or hydrogen chloride.

During steady state operation, pressure drop increases due to progressive fouling (e.g., in piping connected to the exit of the phosgenation mixer) is compensated for by decreased pressure drop in the phosgenation mixer over a time period divided into a first period of time $T_1$ and a second period of time $T_2$ that is subsequent to the first period of time $T_1$. Further, during the first period of time $T_1$ an amine concentration of the one or more amines in the amine-in-solvent stream is lower than during the period of time $T_2$. Also, during the period of time $T_1$ a PAR value in the phosgenation mixer is lower than during the period of time $T_2$. The changes in amine concentration and PAR values may be made in multiple stages, such that the overall operation period may be divided into time periods $T_1$ to $T_n$, where n is an integer from 2 to 1000 (e.g., 2 to 500, 2 to 100, 2 to 50, 2 to 20, etc.). For each subsequent time period $T_{n-1}$ and $T_n$, both the amine concentration and PAR value are changed, e.g., both are increased by individual increments. For example, the amine concentration and PAR value are first increased at the start of the time period $T_{n-1}$ and then increased a second time at the start of the time period $T_n$. The overall operation period may be divided into time periods $T_1$ to $T_n$, may define the full steady state operation time for the system before it is determined a cleaning operation is desired.

The realized amine side pressure drop in the phosgenation mixer may depend on various factors. In exemplary embodiments, the realized amine side pressure drop over the operation period divided into time periods $T_1$ to $T_n$ may be from 1 bar to 50 bar (e.g., 1 bar to 20 bar, 1 bar to 10 bar, 1 bar to 5 bar, etc.)

When referring to changing amine concentration in an amine-in-solvent stream, the concentration may be increased in individual increments in the range from 0.2% to 3.0% (e.g., 0.5% to 2.0%, 0.5% to 1.5%, 0.8% to 1.2%, etc.). Each subsequent individual incremental value may be the same or different from the prior value, e.g., though still within the range from 0.2% to 2.0%. For example, for each subsequent change in amine concentration, the increase may be from 0.2% to 2.0% (as an increase in the actual amine concentration), until it is determined that a cleaning operation is sought to address fouling. After such cleaning operation, the system operation can revert back to the initial amine concentration and proceed with the increasing by increments as fouling occurs again. By concentration it is meant mass percentage, i.e., mass percent of amine. To change the amine concentration, the solvent flow rate for forming the amine-in-solvent inlet stream is changed at a rate to allow for the corresponding change in the amine concentration. The amount of change in the solvent flow rate depends on the overall flow rate of the amine-in-solvent stream.

When referring to changing the PAR values, the values may be increased in individual increments in the range from 0.05 to 1.00 (e.g., 0.05 to 0.50, 0.05 to 0.30, 0.05 to 0.25, etc.). Each subsequent individual incremental value may be the same or different from the prior value, e.g., though still within the range from 0.05 to 0.50. For example, for each subsequent change in PAR value, the increase may be from 0.05 to 0.50, until it is determined that a cleaning operation is sought to address fouling. After such cleaning operation, the system operation can revert back to the initial PAR value and proceed with the increasing by increments as fouling occurs again. To change the PAR values, the phosgene inlet stream flow rate is increased to allow for the corresponding changes in the PAR value. The amount of change in the phosgene inlet stream flow rate depends on the overall flow rate of the phosgene stream and the amine-in-solvent stream.

EXAMPLES

Figure 3:
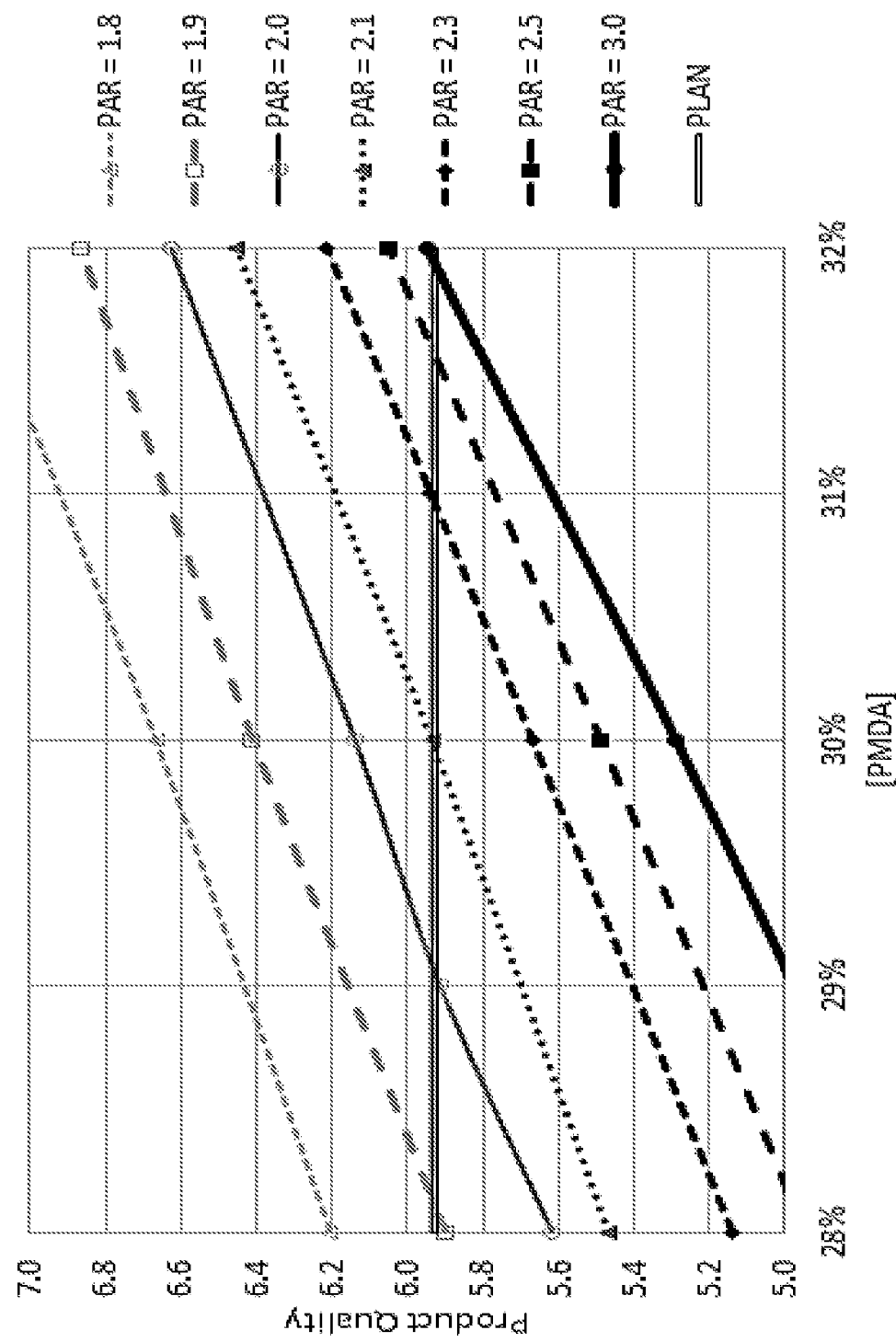
FIG. 3 illustrates a graphical representation of Examples showing Quality Values for varying PMDA concentrations and PAR values, and the horizontal double line represents the desired change in operating conditions to maintain a relatively constant Quality Value.
Figure 4:
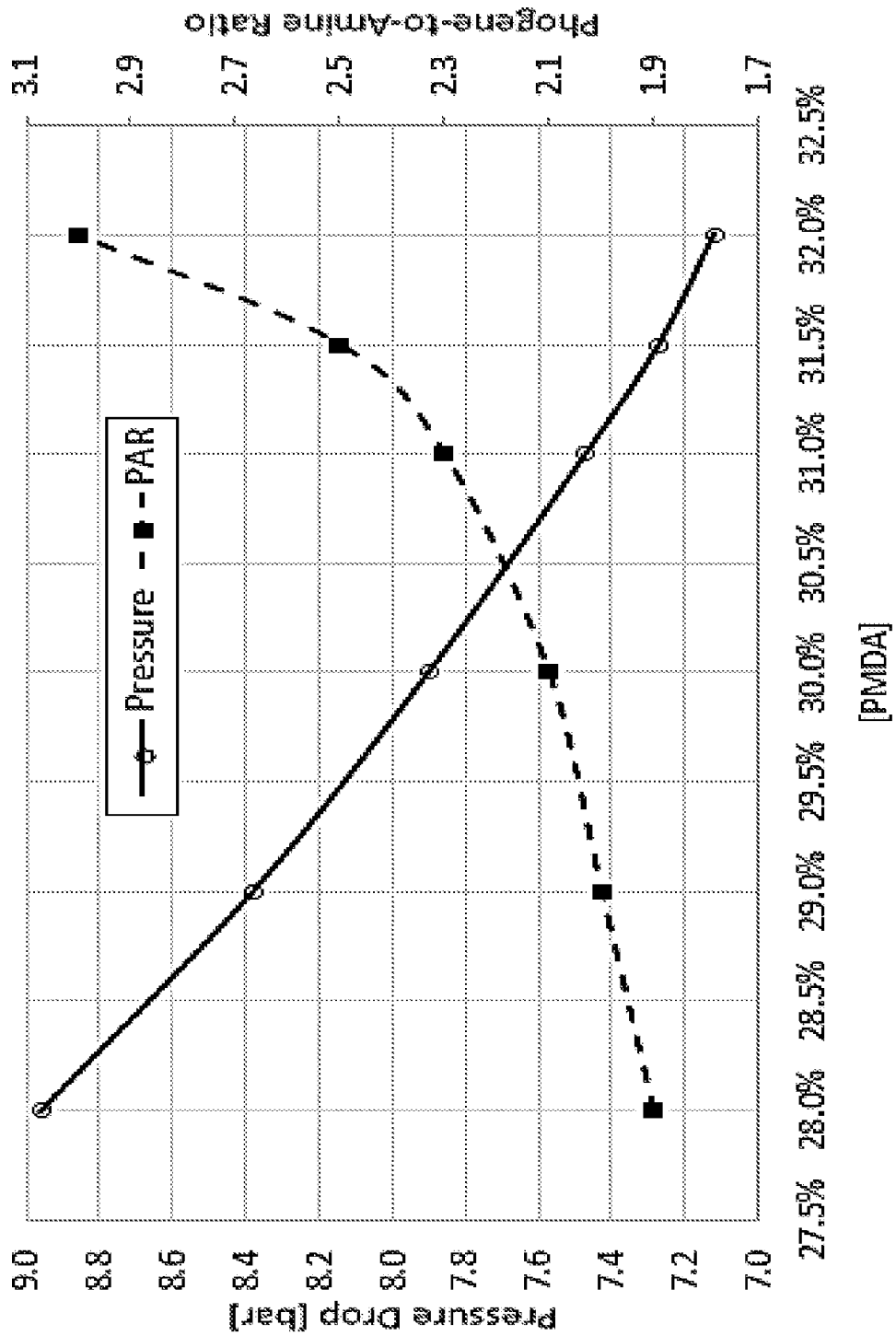
FIG. 4 illustrates a graphical representation of Examples showing phosgenation mixer Pressure Drop (amine side) and PAR value variation while operating the system to maintain a relatively constant Quality Value.

Examples are based on preparing isocyanates using a phosgenation process and phosgenation mixer according to embodiments and are discussed with respect to FIGS. 3 and 4. The Examples are prepared to consider both (1) the relationship between quality values, amine concentration (also referred to herein as PMDA concentrations) in an amine-in-solvent stream, and PAR values; and (2) the relationship between initially higher pressure drop and PAR values, in a process for preparing isocyanates. For the Examples, the resultant final product includes PMDI along with impurities and can be referred to as a PMDI product. The final product is the isocyanate based product from which excess unreacted phosgene, HCl, and/or solvent has been separated out, which is distinguished from the product that exists the phosgenation mixer.

With respect to the Examples, FIG. 3 illustrates a graphical representation showing Quality Values for varying PMDA concentrations and PAR values. The horizontal double line in FIG. 3 represents the desired change in operating conditions, with respect to PMDA concentration and PAR values that lead to a relatively constant Quality Value and a relatively constant production rate. FIG. 4 illustrates a graphical representation that is taken along the horizontal double line in FIG. 3, of Pressure Drop (also referred to amine side pressure drop for the phosgenation mixer) and PAR variation, while at steady state.

The amine-side Pressure Drop is represented by the descending solid line in FIG. 4, which is decreased by decreasing the solvent flow rate for the amine-in-solvent inlet stream and leads to an increase in amine concentration in the amine-in-solvent inlet stream. The amount of solvent in amine-in-solvent inlet stream is reduced without changing the net PMDA flow, such that the amine concentration is relatively increased by decreasing the solvent flow. The amine (PMDA) concentration is mass fraction of amine in the amine-in-solvent stream. The Pressure Drop, is measured as a difference between a first point and a second point. Referring to FIG. 1, the first point is measured in the amine-in-solvent inlet stream upstream of the phosgenation mixer at the second pressure point P2 and the second point is measured in downstream of the phosgenation mixer at the fifth pressure point P5.

The fouling pressure drop is separate from the Pressure Drop associated with the amine-side of phosgenation mixer pressure. The fouling pressure drop is measured as a difference between the second point and a third point. Referring to FIG. 1, the second point is measured in downstream of the phosgenation mixer at the fifth pressure point P5 and the third point is measured in the separator at the sixth pressure point P6. Isocyanate production systems are by nature inherently fouling processes, such that over a period of several weeks at least the downstream piping collects solids, which is referred to as fouling. The fouling reduces the diameter of the piping and changes the surface properties, thus increasing the velocity of the mixture therewithin and increasing the pressure drop in that piping. The fouling pressure drop can be measured across the pipe connecting the phosgenation mixer to a downstream separator. The total pressure drop in the system may be calculated as a difference between the Pressure Drop (i.e., amine side pressure drop) and the downstream fouling pressure drop.

The ascending dashed line in FIG. 4 is the PAR value, which is increased by increasing the phosgene flow rate and is raised to maintain the relatively constant Quality Value. The Quality Value is associated with loss of isocyanate groups to certain by-products, which are formed in a process of forming isocyanates such as polymeric methylene diphenyl diisocyanate (PMDI) and may be used as a basis for describing a purity level of a resultant product. The Quality Value for FIG. 3 is expressed as a weight percentage of a combined total weight of uratomine and/or uretondione based by-products in the final product. The quality value may range from 0 wt % to 30.0 wt %. With respect to FIG. 3, a quality value range of 5.0 wt % to 7.0 wt % is provided. Further, as shown in FIG. 3, the Quality Value can be adjusted by changing the amine concentration in the amine-in-solvent inlet stream and the PAR values. The amine concentration is increased by decreasing the solvent flow rate for the amine-in-solvent inlet stream, and conversely amine concentration can be decreased by increasing the solvent flow. The PAR value is increased by increasing the phosgene inlet stream flow rate, and conversely PAR value may be decreased by decreasing the phosgene inlet stream flow rate.

In the Examples, a pilot scale isocyanate production system is operated to maintain both a relatively constant Production Rate of 0.53 kg/s of the final product and a relatively constant Quality Value of approximately 5.9. Steady state operations for making the final product include an initial amine-in-solvent inlet stream with a flow rate of approximately 0.4 kg/s. The initial amine concentration (i.e., PMDA concentration) is 28 wt %, based on a total weight of the amine-in-solvent inlet stream. The phosgene inlet stream has a flow rate that is variable from 0.2 to 0.5 kg/s and a phosgene concentration equal to or greater than 99 wt %, based on a total weight of the phosgene stream). The Examples take advantage of the initially higher Pressure Drop, which is maintained at a relatively higher level due to the diameter of a single jet opening that is approximately 3.9 mm. In the phosgenation mixer, the Pressure Drop available from the amine side imparts energy to mix the phosgene and amine streams. Further, during steady state operation the Pressure Drop is decreased to compensate for the fouling pressure drop. In the Examples, the goal is to maintain the total pressure drop as relatively constant.

For the Examples, the amine-in-solvent and phosgene streams are mixed in a shear mixing apparatus as discussed in U.S. Pat. No. 7,901,128. Embodiments, may be based on other mixing apparatuses, e.g., as directed toward achieving even higher initial pressure drop and/or energy savings. In order to take advantage of the maximum pressure drop available on the amine side as fouling occurs with respect to the phosgenation mixer and piping, the pilot plant is operated by first increasing the PMDA concentration (by decreasing the solvent flow rate) and then within a time period of one minute increasing the PAR value (by increasing the phosgene inlet stream flow rate). In exemplary embodiments, the PAR value may be changed first, the PMDA concentration or PAR may be changed a few minutes to a one hour in advance of changing the respective other of the PMDA concentration or PAR value, and/or the PMDA concentration and PAR value may be simultaneously changed. Using this strategy, both a constant production rate and Quality Value may be maintained.

With respect to the Examples, it is possible to operate the exemplary pilot plant at exemplary PMDA concentrations ranging from approximately 28% to 32%, PAR value ranging from approximately 1.8 to 3.0, and Pressure Drop from 9.0 bar to 7.1 bar. The actual operating ranges with respect to PMDA concentration, PAR values, and Pressure Drop may be varied at a full scale production plant.

As can be derived from FIG. 3, to maintain a relatively constant Quality Value, plant operation should be modified so as to move horizontally on the graphic representation shown in FIG. 3. For example, when the system is clean, PMDA concentration may be set at approximately 28% and the PAR value may be set at approximately 1.9, to achieve the Quality Value of approximately 5.9. As fouling occurs, the PMDA concentration may be increased to approximately 29% and the PAR value may be increased to approximately 2.0, to maintain the Quality Value of approximately 5.9. It is seen after fouling has substantially increased, the PMDA concentration can be increased to approximately 32% and the PAR value may be increased to approximately 3.0, while still being able to maintain the Quality Value of approximately 5.9. Referring to FIG. 4, using such an operation procedure, the subsequent increases in PMDA concentration allow for Pressure Drop to decrease in the phosgenation mixer to compensation for the fouling pressure drop increase in the downstream piping. Further, to maintain a relatively constant production rate, while varying the amine concentration and the associated Pressure Drop, the PAR values are increased as the Pressure Drop decreases.

Accordingly, as the downstream piping begins to foul, the PMDA concentration may be increased to compensate for the increased pressure drop in the system due to fouling and to maintain the predetermined Quality Value. Further, the PAR value would be increased to maintain the predetermined production rate. This combination of PMDA concentration and PAR values could allow a plant to be run at relatively constant production quality and production rate, even as fouling increases.

The invention claimed is:

1. A process for preparing an isocyanate product, the process comprising:
   providing a phosgene inlet stream and an amine-in-solvent inlet stream to a phosgenation mixer, the amine-in-solvent inlet stream including one or more amines and one or more inert solvents; and
   during steady state operation compensating for a fouling pressure drop increase by decreasing a pressure drop in the phosgenation mixer over a time period divided into at least a first period of time $T_1$ and a second period of time $T_2$ that is subsequent to the first period of time $T_1$, during the second period of time $T_2$ an amine concentration of the one or more amines in the amine-in-solvent stream is higher than during the first period of time $T_1$, and during the second period of time $T_2$ a phosgene-to-amine ratio value in the phosgenation mixer is higher than during the first period of time $T_1$.

2. The process as claimed in claim 1, wherein the amine concentration is increased for the second period of time $T_2$ by decreasing a solvent flow rate for the amine-in-solvent inlet stream.

3. The process as claimed in claim 1, wherein the phosgene-to-amine ratio value is increased by for the second period of time $T_2$ by increasing a flow rate of the phosgene inlet stream.

4. The process as claimed in claim 1, wherein an amine concentration for the second period of time $T_2$ is greater by an amount from 0.2% to 3.0% relative to an amine concentration for the first period of time $T_1$.

5. The process as claimed in claim 1, wherein a phosgene-to-amine ratio value for the second period of time $T_2$ is greater by an amount from 0.05 to 1.00 relative to a phosgene-to-amine ratio value for the first period of time $T_1$.

6. The process as claimed in claim 1, wherein the phosgenation mixer includes one or more jet openings having a diameter from 1 mm to 10 mm for the amine-in-solvent inlet stream.

7. The process as claimed in claim 1, wherein the fouling pressure drop is correlated with at least frictional pressure drop in a piping that connects the phosgenation mixer to a downstream separator.

8. The process as claimed in claim 1, wherein the pressure drop in the phosgenation mixer is correlated with at least adjustments in the composition of the amine-in-solvent inlet stream.

9. The process as claimed in claim 1, wherein the isocyanate product is polymeric methylene diphenyl diisocyanate.

10. The process as claimed in claim 1, wherein during the time period a relatively constant isocyanate product production rate and a relatively constant quality value are maintained, the quality value being a measure of the loss of isocyanate groups by the formation of specific by-products.

* * * * *